United States Patent

Nissan

[11] Patent Number: 5,842,862
[45] Date of Patent: Dec. 1, 1998

[54] ENDODONTIC TOOL

[76] Inventor: Roni Nissan, 1006 Henrietta Ave., Huntingdon Valley, Pa. 19006

[21] Appl. No.: 756,403

[22] Filed: Nov. 27, 1996

[51] Int. Cl.⁶ .................................................. A61C 5/02
[52] U.S. Cl. ............................................................. 433/102
[58] Field of Search .................................. 433/102, 165, 433/224; 606/80, 85; 407/59

[56] References Cited

U.S. PATENT DOCUMENTS

| | | | |
|---|---|---|---|
| 1,067,015 | 7/1913 | Fowler | 433/102 |
| 1,307,446 | 6/1919 | Kerr | 433/102 |
| 4,260,379 | 4/1981 | Groves et al. | 433/102 |
| 5,213,499 | 5/1993 | Levy | 433/102 |

FOREIGN PATENT DOCUMENTS 120542  10/1984  European Pat. Off. ................ 433/165

OTHER PUBLICATIONS

Unitek brochure, Unitek Corporation, Nov. 1983.

*Primary Examiner*—Cary E. O'Connor
*Attorney, Agent, or Firm*—William H. Eilberg

[57] ABSTRACT

A cutting element for an endodontic tool is made from an elongated member having a plurality of notches formed along the length of the member. The member is twisted into a helical pattern. The twisted member defines a cutting element which combines the best properties of a conventional dental file, a reamer, and a Hedstrom file, in a single instrument. The number and depth of the notches can be varied, to control the flexibility of the cutting element. Thus, the instrument can be made of a hard metal, such as stainless steel, but the instrument can still be made flexible by proper choice of the dimensions of the notches. The shape of the notches can also be varied to provide an instrument which cuts only during a "push" stroke or a "pull" stroke. The invention saves time and reduces the cost of dental procedures, by providing a tool which can be used in place of three tools of the prior art.

3 Claims, 3 Drawing Sheets

ENDODONTIC TOOL

BACKGROUND OF THE INVENTION

This invention relates to the field of dentistry, and in particular, to the field of endodontics. The invention comprises an endodontic tool which performs the functions of several different tools of the prior art.

In a root canal procedure, the dentist removes inflamed tissue and debris from the canal, prior to filling the canal with an inert filling material. In performing this procedure, the dentist must gain access to the entire canal, shaping it as necessary. But root canals normally are very small in diameter, and they are usually quite curved. It is therefore very difficult to gain access to the full length of a root canal.

Many tools have been designed, in the prior art, to perform the difficult task of cleaning and shaping root canals. In general, these tools fall into three major categories.

The first category includes files. As understood in the dental field, a file is a twisted wire, typically having either a triangular or a rectangular or square cross-section. Dental files often have about 1–2 flutes per millimeter of length along the file. By definition, a file is used with a push-pull motion; that is, a file is inserted into the canal, and moved rapidly in and out, so as to scrape out the dentin.

The second category includes reamers. A reamer is also a twisted wire, generally with a triangular cross-section. At one time, a file and a reamer could be distinguished by the shape of their cross-sections, but the files and reamers that are presently manufactured may often have the same cross-sectional shapes. The major difference between a file and a reamer is in the number of twists per unit length, the reamer having fewer twists, typically about ¼ or ½ flutes per millimeter. A reamer is essentially a drill, and is used in the root canal with a reaming motion, i.e. an inward rotating motion.

The third category includes Hedstrom files. A Hedstrom file is made by machining a plurality of spiraling flutes into the shaft of a piece of round wire. The flutes of a Hedstrom file are very sharp, but the instrument is fragile. The Hedstrom file is used in the canal with a filing motion, i.e. a push-pull motion.

All of the instruments described above have advantages and disadvantages. A Hedstrom file is very sharp, but because it is fragile, one cannot twist or rotate it in the root canal. A regular file can be twisted, but only with difficulty. A reamer is made for twisting, but it is not nearly as sharp as a Hedstrom file. A regular file is less fragile, but it is often not sharp enough for many desired uses.

Thus, none of the above-described instruments is suitable for all uses. For this reason, the dentist must usually be prepared to use two or three different instruments in a single procedure.

Another problem with the above-described instruments is their lack of flexibility. Because most root canals are curved, the tools used to clean them must be flexible. One solution to the problem has been to make the tool of a nickel-titanium alloy (NiTi). The use of NiTi does increase the flexibility of the tool, but it also reduces its rigidity. NiTi is a soft metal that can become dull very quickly. A tool made of NiTi cannot be used as aggressively as one made of a stronger material, such as stainless steel. Moreover, NiTi is relatively brittle.

The present invention provides an endodontic tool which combines the best features of the various tools of the prior art. The tool of the present invention is flexible, yet strong enough to be used aggressively. The invention reduces the number of tools needed by the dentist, in a single procedure.

SUMMARY OF THE INVENTION

The present invention comprises an endodontic tool having a unique cutting element. In a preferred embodiment, the cutting element has a generally rectangular cross-section, defining four longitudinal surfaces and four corners. The cutting element has notches formed in its four corners. The notches formed in one corner are staggered relative to those formed in adjacent corners. The cutting element is twisted so that each longitudinal surface defines a helix.

In one embodiment, the notches formed in the tool include two interior surfaces, having a generally triangular shape, and a connecting surface which is perpendicular to the two interior surfaces. The triangular shapes of the interior surfaces define sharp points which increase the effectiveness of the tool in scraping and cutting.

In another embodiment, the notches include only two surfaces, both of which are triangular, but only one of which defines a sharp point. In this embodiment, the tool will scrape debris when it is moved in one direction, but not when it is moved in the opposite direction.

The tool of the present invention has the sharpness of a Hedstrom file, although it is at least as strong as a conventional file. Because it includes helical surfaces, the tool of the present invention can also be used in dental procedures requiring a reamer. The notches formed in the cutting element give flexibility to the tool, even when the tool is made of a hard material such as stainless steel. Thus, one can insert the tool into narrow and curved canals, while still being able to maneuver the tool aggressively.

Another aspect of the invention is its use of a pear-shaped handle attached to the cutting element. The pear-shaped handle provides the operator with a better fulcrum with which to push and pull the tool.

The present invention therefore has the primary object of providing an improved endodontic tool which combines the best features and advantages of a file, a reamer, and a Hedstrom file.

The invention has the further object of providing an endodontic tool which is flexible but strong.

The invention has the further object of reducing the cost and complexity of dental procedures.

The invention has the further object of reducing the number of tools which a dentist must use during a single procedure.

The invention has the further object of providing an endodontic tool which is flexible but not brittle.

The invention has the further object of providing an endodontic tool which can be inserted into narrow and curved canals, but which can also be maneuvered aggressively.

The invention has the further object of providing an improved handle for an endodontic tool.

The reader skilled in the art will recognize other objects and advantages of the present invention, from a reading of the following brief description of the drawings, the detailed description of the invention, and the appended claims.

DETAILED DESCRIPTION OF THE INVENTION

Figure 1:
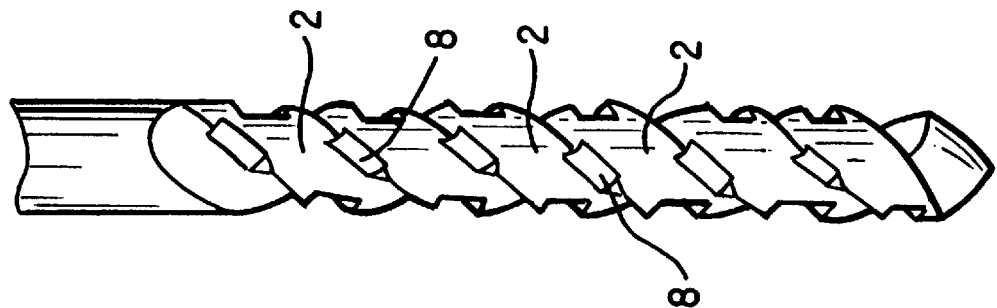
FIG. 1 provides a perspective view of a notched member used to form the cutting element of the endodontic tool of the present invention.

FIG. 1 provides a perspective view of a member used to form the cutting element of the endodontic tool of the present invention. In the embodiment of FIG. 1, member 1 has a generally rectangular cross-section. Member 1 therefore includes four longitudinally-disposed surfaces, two of which are visible in FIG. 1 and which are designated by reference numeral 2. The member also has two end surfaces, one of which is visible in FIG. 1, and which is designated by reference numeral 4. The surfaces of member 1 define four corners or edges, three of which are visible in FIG. 1, and which are designated by reference numerals 5, 6, and 7.

Member 1 has a plurality of notches formed in its corners. The notches, designated generally by reference numeral 8, are disposed along the length of each of the corners. The notches formed along one corner are staggered relative to the notches formed along adjacent corners.

In the preferred embodiment, as shown in FIG. 1, each of the notches includes two interior surfaces 9 which have a generally triangular shape, and which are parallel to the end surfaces of member 1. Each of the notches also includes a connecting surface 10 which is perpendicular to the two interior surfaces. The triangular shape of each interior surface 9 defines a point 11.

It should be understood that the rear view of member 1 is identical to the front view shown in FIG. 1. That is, in the embodiment of Figure 1, member 1 is symmetrical, and the corner which is not visible in the view of FIG. 1 also has notches substantially identical to the notches illustrated.

Figure 2:
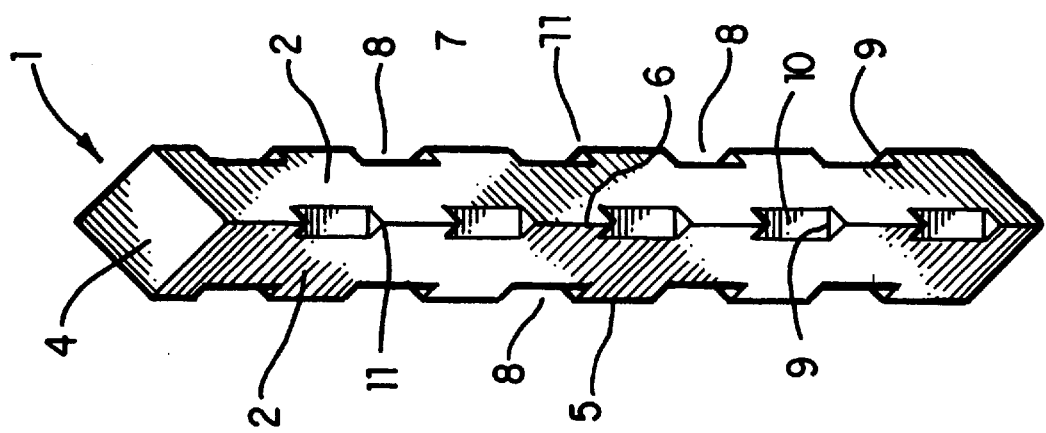
FIG. 2 provides a perspective view of the cutting element of the present invention.

FIG. 2 provides a perspective view of the cutting element of the tool of the present invention. The cutting element of FIG. 2 is simply member 1 of FIG. 1 twisted into a helix. FIG. 2 shows the longitudinal surfaces 2 which now form generally helical paths. The now-helical surfaces 2 have edges which were formerly the corners of FIG. 1. Notches 8 are formed in these edges, by virtue of the twisting of the structure shown in FIG. 1 to produce the structure of FIG. 2. The twisting process modifies the orientation of the notches, as indicated in FIG. 2.

To make a finished tool from the cutting element shown in FIG. 2, one would attach a handle to the cutting element. The handle is not shown. Also, the cutting element can be formed with a taper, as discussed below.

Because the diameter of a root canal generally becomes smaller as one moves more deeply into the tooth, towards the apex of the root, the endodontic tools of the prior art have been generally formed with a corresponding taper. That is, the diameter of the cutting element decreases towards the distal end of the tool. A typical amount of taper is 0.02 mm per 1 mm length along the tool. The latter taper is designated in the field as a taper of 0.02. The tool of the present invention can be formed with the standard taper of 0.02, or it can be formed with tapers of 0.03, 0.04, 0.05, or various other amounts of taper. Note also that the standard length of the cutting element of the tool is 16 mm, but the present invention is not limited to this length.

The number and depth of the notches can be varied. In the embodiment of FIG. 1, the number of notches formed along each corner is the same, and each notch has the same depth. But the cutting element can be formed with unequal numbers of notches on the respective corners, and/or the notches can be formed with different depths. By so controlling the number and depth of the notches, one can precisely control the flexibility of the tool. The cutting element can therefore be formed of stainless steel, or other hard metal, to enable the tool to be maneuvered aggressively. The tool is still flexible because of the notches which reduce the effective thickness of the metal used to form the cutting element.

In one embodiment, wherein the cutting element is 16 mm long, the notches can be formed at intervals of about 0.5–1.0 mm or more. But the latter dimensions are only examples, and should not be deemed to limit the invention in any way. Not only can the number and depth of the notches be varied, but the amount of offset of the notches on one corner, relative to the notches on adjacent corners, can also be varied. Of course, the number of flutes per unit length of the cutting element can also be varied.

The notches substantially increase the sharpness of the cutting edge of the tool. The points 11 formed by the triangular surfaces, when used with a filing or reaming motion, will engage the root canal walls and remove dentin very effectively.

Figure 3:
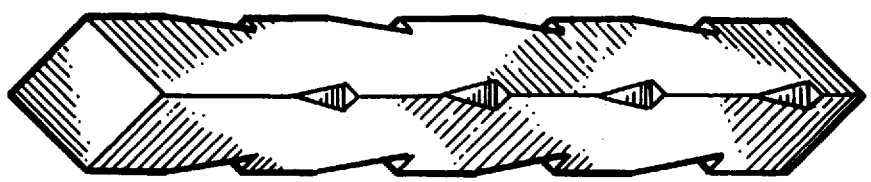
FIG. 3 provides a perspective view of a notched member used to form an alternative embodiment of the present invention.
Figure 4:
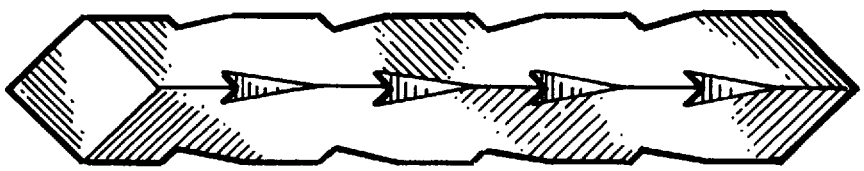
FIG. 4 provides a perspective view of a notched member used to form still another alternative embodiment of the present invention.

In the embodiment of FIGS. 1 and 2, the notches can be considered "two-sided", insofar as each notch includes two points 11, and the tool will cut both when it is pushed and when it is pulled. FIGS. 3 and 4 show alternatives wherein the notches are one-sided. For convenience of illustration, FIGS. 3 and 4 show the cutting element before it has been twisted into its final form, and without a taper; it is understood that the final product can be twisted in a manner similar to that indicated by FIG. 2, and that it may be tapered.

In FIG. 3, the notches include a triangular surface which is parallel to the end surfaces of the cutting element. But the notches have only one other surface, also triangular, which surface is oblique relative to both the end surfaces and the longitudinal axis of the cutting element. FIG. 4 is similar to FIG. 3, except that the orientation of the notches is reversed. However, when the tool is finished, it may be formed with a taper. If the tools of FIGS. 3 and 4 taper down, in the direction of their distal ends (the ends which extend farthest into the canal), the two tools will be distinguishable. Also, the finished tool includes a handle, which would further distinguish the tool of FIG. 3 from that of FIG. 4.

It is apparent from FIGS. 3 and 4 that the one-sided notches will cut preferentially in one direction, either when the tool is pushed or pulled. For the embodiment of FIG. 3, the tool will cut only on a "pull" stroke, i.e. while filing towards the outside of the canal, and it is inactive when the tool is pushed into the canal. As a result, less dentin debris is packed at the apical area and more dentin debris comes out of the canal. For the embodiment of FIG. 4, the tool does the exact opposite, and it could be used after the root canal has already been cleaned out, when the dentist wants to pack dentin shavings into the apical part of the canal to create an apical stop. A stop at the apex of the root canal prevents the root canal filling from flowing into the underlying tissue, thereby preventing contamination, irritation, and/or infection of the tissue. Notches of still other shapes can be used, within the scope of the present invention.

Figure 5:
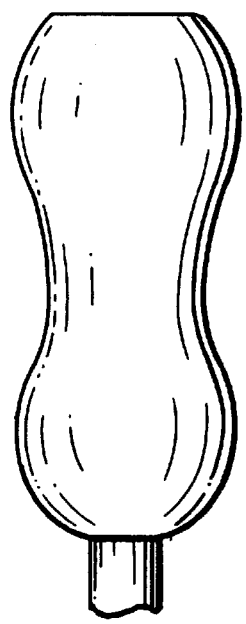
FIG. 5 provides an elevational view of a prior art handle for an endodontic tool.
Figure 6:
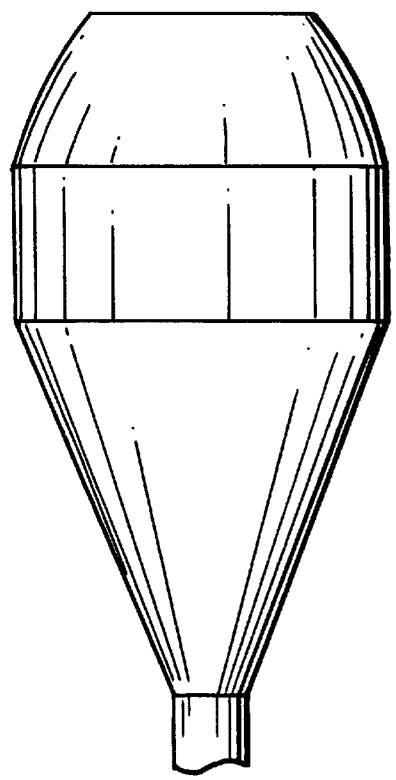
FIG. 6 provides an elevational view of a handle for an endodontic tool, the handle being made according to the present invention.

The present invention also includes an improved handle for an endodontic tool. The handles used in the prior art are exemplified by FIG. 5, which shows a handle having round crosscuts with a generally cylindrical shape. The preferred handle of the present invention is shown in FIG. 6. This handle is generally pear-shaped, and has a larger maximum diameter and a longer length than the handles of the prior art. The farther the distance from the cutting element, the greater the diameter of the handle. The handle tapers down substantially to match the diameter of the cutting element.

The handle shown in FIG. 6 improves the operator's grip on the handle, and increases the efficiency of the tool by providing a better fulcrum. The pear shape makes it easier to push and pull the tool because it offers the operator a better fulcrum and grip.

Figure 7:
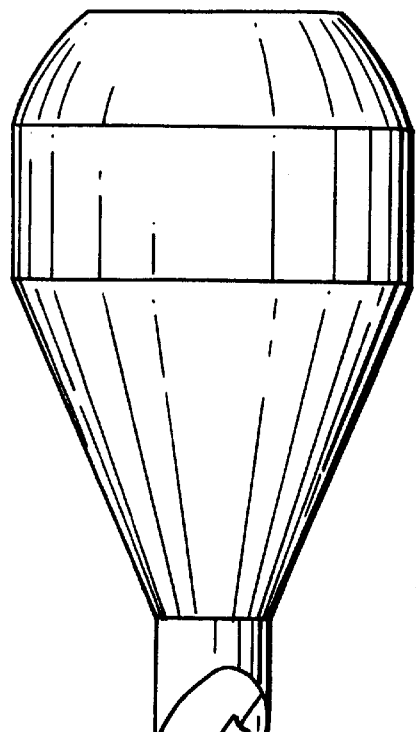
FIG. 7 provides an elevational view of the tool of the present invention.
Figure 7:

FIG. 7 illustrates a compete tool made according to the present invention, including the pear-shaped handle and the cutting element described above.

The tool of the present invention need not include both the novel handle and the novel cutting element. Either or both of these features may be present in the tool.

The present invention therefore has the following important advantages, as compared with endodontic tools of the prior art:

1) The cutting element of the present invention is essentially a dental file which has the sharpness of a Hedstrom file. The instrument can be safely rotated in the canal using a reaming motion or a filing motion, unlike the Hedstrom file, where rotational motion is not desirable because of the risk of fracturing the instrument. Thus, the present invention provides a tool which essentially combines the three conventional tools into one, thus saving time and expense in dental procedures.

2) The notches on the cutting element of the present invention can be deepened with each increase in instrument size, thereby increasing the flexibility of the larger instrument, even when the tool is made of a relatively hard metal such as stainless steel.

3) The notches formed in the cutting element increase the volume of dentin debris that can be removed from the canal.

4) The tool is not unduly brittle or soft.

5) The tool maximizes the usable surface of the cutting element relative to the surface of the canal, enabling the dentist to use the tool more efficiently than tools of the prior art.

6) The tool provides a handle which enhances the ability of the operator to push and pull the tool.

The cutting element need not have a rectangular or square cross-section. The element could have a rhomboid (diamond-shaped) cross-section, or an S-type or U-type cross-section, or other shapes. The invention is not limited to one particular cross-sectional shape.

In the preferred embodiment shown in the drawings, the notches are oriented generally parallel to the longitudinal axis of the cutting element. But the notches could be oriented in other directions. The angle between the notches and the longitudinal axis could be 0°, or 45°, or 90°, or some other angle. The invention is not limited by the angle of the notches.

The tool of the present invention can be provided with either a cutting or non-cutting tip. That is, the distal end of the tool can be either sharp or blunt. Both forms of tip are compatible with the present invention.

The present invention is not limited to particular materials. As noted above, the tool of the present invention, if made of stainless steel, will still have some flexibility due to the notches formed in the cutting element. On the other hand, if the tool of the present invention is made of NiTi, it will still be much sharper than comparable NiTi tools of the prior art, while having the advantages of NiTi. In other words, one feature of the present invention is that it can overcome a disadvantage of NiTi, namely its softness. By making the instrument sharper, the present invention renders a NiTi instrument much more efficient.

The tool of the present invention can be fabricated for manual use, i.e. with a handle, or with an attachment to a dental drill for use with a machine.

The tool of the present invention may be fabricated in any or all of the standardized sizes (diameters) and lengths which are used in the dental field. The invention is not limited, however, to any particular diameter or length.

Although the invention has been described with regard to certain preferred embodiments, many variations are possible, as indicated in the foregoing description. These variations, and others which should be apparent to those skilled in the art, should be considered within the spirit and scope of the following claims.

What is claimed is:

1. A cutting element for an endodontic tool, the cutting element comprising:

a) a member having a generally polygonal cross-section, the cross-section defining four corners, the member having a length, and the member having four longitudinally-disposed surfaces extending along said length, b) the member having a plurality of spaced apart notches formed along at least some of said four corners, c) the member being twisted such that the surfaces are arranged in a generally helical pattern, wherein the member has two end surfaces, and wherein the notches include a first interior surface which is parallel to said end surfaces and a second interior surface which is oblique to said end surfaces, wherein the notches comprise means for cutting preferentially in a single direction.

2. The cutting element of claim 1, wherein the notches are formed along all four of said corners.

3. The cutting element of claim 1, wherein the notches formed along one of said corners are staggered relative to the notches formed along an adjacent corner.

* * * * *